United States Patent [19]

Ogura

[11] Patent Number: 5,900,640

[45] Date of Patent: May 4, 1999

[54] IMAGE READING APPARATUS

[75] Inventor: Nobuhiko Ogura, Kanagawa-ken, Japan

[73] Assignee: Fuji Photo Film Co., Ltd., Kanagawa-ken, Japan

[21] Appl. No.: 08/874,342

[22] Filed: Jun. 13, 1997

[30] Foreign Application Priority Data

Jun. 18, 1996 [JP] Japan .................................. 8-155913

[51] Int. Cl.⁶ .................................................. G03B 42/02
[52] U.S. Cl. ........................... 250/583; 250/585; 250/586
[58] Field of Search ..................... 250/585, 583, 250/586

[56] References Cited

U.S. PATENT DOCUMENTS

| | | |
|---|---|---|
| 5,083,023 | 1/1992 | Miyagawa . |
| 5,307,148 | 4/1994 | Kambara et al. . |
| 5,427,910 | 6/1995 | Kamentsky et al. . |
| 5,459,325 | 10/1995 | Hueton et al. ........................ 250/458.1 |
| 5,502,465 | 3/1996 | Agano . |
| 5,528,050 | 6/1996 | Miller et al. ........................... 250/585 |

FOREIGN PATENT DOCUMENTS

| | | |
|---|---|---|
| 0666487 A2 | 8/1995 | European Pat. Off. . |
| 55-12429 | 1/1980 | Japan . |
| 55-116340 | 9/1980 | Japan . |
| 55-163472 | 12/1980 | Japan . |
| 56-11395 | 2/1981 | Japan . |
| 56-104645 | 8/1981 | Japan . |
| 59-15843 | 1/1984 | Japan . |
| 61-51738 | 3/1986 | Japan . |
| 61-93538 | 5/1986 | Japan . |
| 1-205148 | 8/1989 | Japan ..................................... 250/585 |
| 1-60782 | 12/1989 | Japan . |
| 1-60784 | 12/1989 | Japan . |
| 4-3952 | 1/1992 | Japan . |
| 6-19014 | 1/1994 | Japan ..................................... 250/586 |
| WO 9201966 | 2/1992 | WIPO . |

*Primary Examiner*—Constantine Hannaher
*Attorney, Agent, or Firm*—Sughrue, Mion, Zinn Macpeak & Seas, PLLC

[57] ABSTRACT

An image reading apparatus includes at least two laser stimulating ray sources for emitting laser beams having different wavelengths, a laser beam scanner for scanning an image carrier carrying an image with the laser beam emitted from a selected one of the laser stimulating ray sources and a light detector for photoelectrically detecting light released from the image carrier, the laser beam scanner being provided with a laser beam transmission portion for transmitting the laser beam therethrough. The image reading apparatus further includes a mirror for reflecting light released from the image carrier to lead it to the light detector. According to the thus constituted image reading apparatus, it is possible to be used for a radiation diagnosis system, an autoradiographic system, an electron microscope detecting system and a radiation diffraction image detecting system using a stimulable phosphor and a fluorescence detecting system and accurately reading an image with a simple structure.

20 Claims, 3 Drawing Sheets

IMAGE READING APPARATUS

BACKGROUND OF THE INVENTION

The present invention relates to an image reading apparatus and, particularly, to such an apparatus comprising a plurality of laser stimulating ray sources for emitting laser beams having different wavelengths and capable of being used for a radiation diagnosis system, an autoradiographic system, an electron microscope detecting system and a radiation diffraction image detecting system using a stimulable phosphor and a fluorescence detecting system and accurately reading an image with a simple structure.

DESCRIPTION OF THE PRIOR ART

There is known a radiation diagnosis system comprising the steps of employing, as a detecting material for the radiation, a stimulable phosphor which can absorb and store the energy of radiation upon being irradiated therewith and release a stimulated emission whose amount is proportional to that of the received radiation upon being stimulated with an electromagnetic wave having a specific wavelength range, storing and recording the energy of radiation transmitted through an object in the stimulable phosphor contained in a stimulable phosphor layer formed on a stimulable phosphor sheet, scanning the stimulable phosphor layer with an electromagnetic wave to excite the stimulable phosphor, photoelectrically detecting the stimulated emission released from the stimulable phosphor to produce digital image signals, effecting image processing on the obtained digital image signals, and reproducing an image on displaying means such as a CRT or the like or a photographic film (see for example, Japanese Patent Application Laid Open Nos. 55-12429, 55-116340, 55-163472, 56-11395, 56-104645 and the like).

There is also known an autoradiography system comprising the steps of employing a similar stimulable phosphor as a detecting material for the radiation, introducing a radioactively labeled substance into an organism, using the organism or a part of the tissue of the organism as a specimen, placing the specimen and a stimulable phosphor sheet formed with a stimulable phosphor layer together in layers for a certain period of time, storing and recording radiation energy in a stimulable phosphor contained in the stimulable phosphor layer, scanning the stimulable phosphor layer with an electromagnetic wave to excite the stimulable phosphor, photoelectrically detecting the stimulated emission released from the stimulable phosphor to produce digital image signals, effecting image processing on the obtained digital image signals, and reproducing an image on displaying means such as a CRT or the like or a photographic film (see for example, Japanese Patent Publication No. 1-60784, Japanese Patent Publication No. 1-60782, Japanese Patent Publication No. 4-3952 and the like).

There are further known an electron microscope detecting system and a radiographic diffraction image detecting system comprising the steps of employing, as a detecting material for an electron beam or radiation, a stimulable phosphor which can absorb and store the energy of an electron beam or radiation upon being irradiated therewith and release a stimulated emission whose amount is proportional to that of the received electron beam or radiation upon being stimulated with an electromagnetic wave having a specific wavelength range, irradiating a metal or nonmetal specimen with an electron beam and effecting elemental analysis, composition analysis or structural analysis of the specimen by detecting a diffraction image or a transmission image, or irradiating the tissue of an organism with an electron beam and detecting an image of the tissue of the organism, or irradiating a specimen with radiation, detecting a radiographic diffraction image and effecting structural analysis of the specimen (see for example, Japanese Patent Application Laid Open No. 61-51738, Japanese Patent Application Laid Open No. 61-93538, Japanese Patent Application Laid Open No. 59-15843 and the like).

Unlike the system using a photographic film, according to these systems using the stimulable phosphor as a detecting material for an image, development using chemical processing becomes unnecessary. Further, it is possible reproduce a desired image by effecting image processing on the obtained image data and effect quantitative analysis using a computer. Use of a stimulable phosphor in these processes is therefore advantageous.

On the other hand, a fluorescence system using a fluorescent substance as a labeling substance instead of a radioactively labeled substance in the autoradiography system is known. According to this system, it is possible to study a genetic sequence, the expression level of a gene and the metabolism, absorption, excretion path and state of a substance introduced into a test mouse and to effect the separation or identification of protein or the estimation of the molecular weight or properties of protein or the like. For example, this system can perform a process including the steps of distributing a plurality of DNA fragments on a gel support by means of electrophoresis after a fluorescent dye was added to a solution containing a plurality of DNA fragments to be distributed or distributing a plurality of DNA fragments on a gel support containing fluorescent dye or dipping a gel support on which a plurality of DNA fragments have been distributed by means of electrophoresis in a solution containing fluorescent dye, thereby labeling the electrophoresis-distributed DNA fragments, exciting the fluorescent dye by a stimulating ray to cause it to release a fluorescent light, detecting the released fluorescent light to produce an image and detecting the distribution of the DNA on the gel support. This system also performs a process including the steps of distributing a plurality of DNA fragments on a gel support by means of electrophoresis, denaturing the DNA, transferring at least a part of the denatured DNA fragments onto a transfer support such as a nitrocellulose support by the Southern-blotting method, hybridizing a probe prepared by labeling target DNA and DNA or RNA complementary thereto with the denatured DNA fragments, thereby selectively labeling only the DNA fragments complementary to the probe DNA or probe RNA, exciting the fluorescent dye by a stimulating ray to cause it to release a fluorescent light, detecting the released fluorescent light to produce an image and detecting the distribution of the target DNA on the transfer support. This system can further perform a process including the steps of preparing a DNA probe complementary to DNA containing a target gene labeled by a labeling substance, hybridizing it with DNA on a transfer support, combining an enzyme with the complementary DNA labeled by a labeling substance, causing the enzyme to contact a fluorescent substrate, transforming the fluorescent substrate to a fluorescent substance having a property to release fluorescent light, exciting the thus produced fluorescent substance by a stimulating ray to release fluorescent light, detecting the fluorescent light to produce an image and detecting the distribution of the target DNA on the transfer support. This fluorescence detecting system is advantageous in that a genetic sequence or the like can be easily detected without using a radioactive substance.

The radiation diagnosis system, the autoradiographic system, the electron microscope detecting system and the radiation diffraction image detecting system using a stimulable phosphor as the image detecting material and the fluorescence detecting system all scan an image carrier such as a stimulable phosphor sheet, a gel support, a transfer support or the like with a stimulating ray and produce an image by detecting light emitted from the image carrier to effect diagnosis or detection. It is therefore advantageous and preferable to constitute an image reading apparatus so as to be usable for any of these systems.

Therefore, an image reading apparatus has been proposed, which is provided with a solid laser stimulating ray source for emitting a laser beam having a wavelength of 635 nm capable of exciting a stimulable phosphor BaFX (X representing a halogen.) for making it usable in the autoradiography systems and an LED for emitting light having a wavelength of 450 nm capable of exciting fluorescent substances used in a fluorescence detecting system for making it usable in the fluorescence detecting system.

This image reading apparatus scans the surface of an image carrier such as a stimulable phosphor sheet, a gel support or a transfer support with a stimulating ray by moving an optical head in which the solid laser stimulating ray source and the LED are built in both main scanning and sub-scanning directions and leads stimulated emission or fluorescent light released from the image carrier by optical fibers fixed to the optical head to a light detector to photoelectrically detect it.

However, it is necessary to move the optical head in both the main scanning direction and the sub-scanning direction at a high speed. Therefore, while it is desirable to use a laser stimulating ray source instead of the LED in order to use a stimulating ray having high intensity and improve the detection sensitivity, it is extremely difficult to install the laser stimulating ray source in the optical head and, as a result, the sensitivity of the image reading apparatus cannot be improved.

Further, U.S. Pat. No. 5,459,325 discloses an image reading apparatus provided with a dichroic mirror for reflecting a stimulating ray emitted from a stimulating ray source, which reads an image by the steps of reflecting the stimulating ray by the dichroic mirror to direct it to an optical head provided with a mirror and a convex lens, reflecting the stimulating ray by the mirror toward the surface of an image carrier such as a gel support or a transfer support carrying a fluorescent image, converging the stimulating ray by the convex lens onto the surface of the image carrier while the optical head is being moved in the main scanning direction and the sub-scanning direction, thereby scanning the whole surface of the image carrier with the stimulating ray, transforming fluorescent light released from the image carrier into parallel light by the convex lens, reflecting the fluorescent light by the mirror, leading the fluorescent light to a light detector via the dichroic mirror and photoelectrically detecting the fluorescent light.

In this image reading apparatus, since the image carrier is scanned with the stimulating ray by moving the optical head provided with the mirror and the convex lens, it is possible to employ a laser stimulating ray source. However, if two or more stimulating ray sources are used for stimulating the image carrier with two or more stimulating rays in this image reading apparatus, the dichroic mirror must be able to reflect all stimulating rays and transmit all fluorescent light released from the fluorescent dyes upon being stimulated with all stimulating rays. However, since the wavelength of fluorescent light released upon stimulation with a certain stimulating ray may overlap the wavelength of another stimulating ray, it is in actual practice necessary for reading an image to provide dichroic mirrors in a number equal to the number of stimulating ray sources and position the dichroic mirror corresponding to the stimulating ray source to be activated in the optical path of the stimulating ray. Therefore, it is indispensable to provide drive means for positioning the dichroic mirror corresponding to the stimulating ray source to be activated in the optical path of the stimulating ray. As a result, the structure of the image reading apparatus becomes complicated and the image reading apparatus becomes larger.

SUMMARY OF THE INVENTION

It is therefore an object of the present invention to provide an image reading apparatus comprising a plurality of laser stimulating ray sources for emitting laser beams having different wavelengths and capable of being used for a radiation diagnosis system, an autoradiographic system, an electron microscope detecting system and a radiation diffraction image detecting system using a stimulable phosphor and a fluorescence detecting system and accurately reading an image with a simple structure.

The above and other objects of the present invention can be accomplished by an image reading apparatus comprising at least two laser stimulating ray sources for emitting laser beams having different wavelengths, laser beam scanning means for scanning an image carrier carrying an image with the laser beam emitted from a selected one of the laser stimulating ray sources and light detecting means for photoelectrically detecting light released from the image carrier, the laser beam scanning means being provided with a laser beam transmission portion for transmitting the laser beam therethrough, the image reading apparatus further comprising mirror means for reflecting light released from the image carrier to lead it to the light detecting means.

In a preferred aspect of the present invention, the laser beam transmission portion of the mirror means is formed by a hole.

In another preferred aspect of the present invention, the laser beam transmission portion of the mirror means is formed by applying a coating capable of transmitting the stimulating ray therethrough onto the mirror.

In a further preferred aspect of the present invention, the at least two laser stimulating ray sources include a first laser stimulating ray source for emitting a laser beam having a wavelength of 633 nm or 635 nm and a second laser stimulating ray source for emitting a laser beam having a wavelength of 470 nm to 480 nm.

In a further preferred aspect of the present invention, the image carrier to be scanned with the laser beam emitted from the first laser stimulating ray source is constituted by a carrier carrying an image of fluorescent substances or a stimulable phosphor sheet containing a stimulable phosphor recording an image selected from the group consisting of a radiation image, an autoradiographic image, a radiographic diffraction image and an electron microscope image of an object and the image carrier to be scanned with the laser beam emitted from the second laser stimulating ray source is constituted by a carrier carrying an image of fluorescent substances.

In a further preferred aspect of the present invention, the image reading apparatus further comprises a third laser stimulating ray source for emitting a laser beam having a wavelength of 530 to 540 nm.

In a further preferred aspect of the present invention, the image carrier to be scanned with the laser beam emitted from the third laser stimulating ray source is constituted by a carrier carrying an image of fluorescent substances.

As termed with respect to the present invention, the phrase "the image carrier carries an image of fluorescent substances" includes the case where the image carrier carries an image of a specimen labeled by a labeling substance and the case where the image carrier carries an image of fluorescent substances obtained by combining an enzyme with a specimen labeled by a labeling substance, causing the enzyme to contact a fluorescent substrate and transforming the fluorescent substrate to a fluorescent substance.

In the present invention, the fluorescent substance employed for labeling a specimen to form an image to be carried in an image carrier and read by stimulating it using a laser beam having a wavelength of from 470 nm to 480 nm may be of any type insofar as it can be stimulated by a laser beam having a wavelength of from 470 nm to 480 nm. However, preferably employed fluorescent substances stimulable by a laser beam having a wavelength of from 470 nm to 480 nm include Fluorescein (C.I. No. 45350), Fluorescein-X indicated by the structural formula (1) shown below, YOYO-1 indicated by the structural formula (2), TOTO-1 indicated by the structural formula (3), YOPRO-1 indicated by the structural formula (4), Cy-3 (registered trademark) indicated by the structural formula (5), Nile Red indicated by the structural formula (6), BCECF indicated by the structural formula (7), Rhodamine 6G (C.I. No. 45160), Acridine Orange (C.I. No. 46005), SYBR Green ($C_2H_6OS$), Quantum Red, R-Phycoerrythrin, Red 613, Red 670, Fluor X, FAM, AttoPhos, Bodipy phosphatidylcholine, SNAFL, Calcium Green, Fura Red, Fluo 3, AllPro, NBD phosphoethanolamine and the like. In the present invention, the fluorescent substance employed for labeling a specimen to form an image to be carried in an image carrier and read by stimulating it using a laser beam having a wavelength of from 633 nm or 635 nm may be of any type insofar as it can be stimulated by a laser beam having a wavelength of from 633 nm or 635 nm. However, preferably employed fluorescent substances stimulable by a laser beam having a wavelength of from 633 nm or 635 nm include Cy-5 (registered trademark) indicated by the structural formula (8), Allphycocyanin and the like. Moreover, in the present invention, the fluorescent substance employed for labeling a specimen to form an image to be carried in an image carrier and read by stimulating it using a laser beam having a wavelength of from 530 nm to 540 nm may be of any type insofar as it can be stimulated by a laser beam having a wavelength of from 530 nm to 540 nm. However, preferably employed fluorescent substances stimulable by a laser beam having a wavelength of from 530 nm to 540 nm include Cy-3 (registered trademark) indicated by the structural formula (5), Rhodamine 6G (C.I. No. 45160), Rhodamine B (C.I. No. 45170), Ethidium Bromide indicated by the structural formula (9), Texas Red indicated by the structural formula (10), Propidium Iodide indicated by the structural formula (11), POPO-3 indicated by the structural formula (12), Red 613, Red 670, Carboxyrhodamine (R6G), R-Phycoerythirin, Quantum Red, JOE, HEX, Ethidium homodimer, Lissamine rhodamine B peptide and the like.

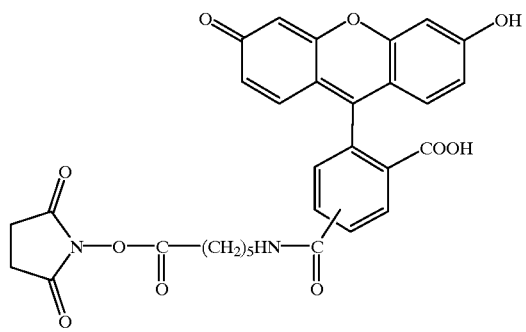

Fluorescein-X (1)

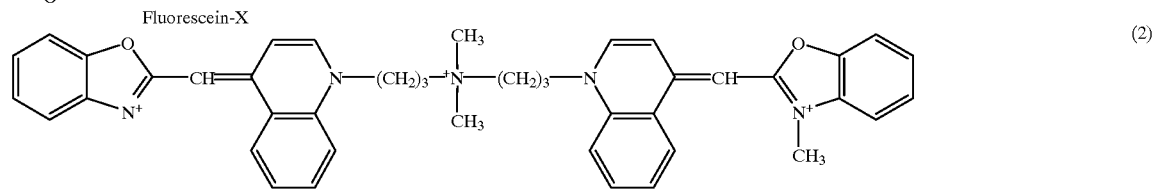

YOYO-1 (2)

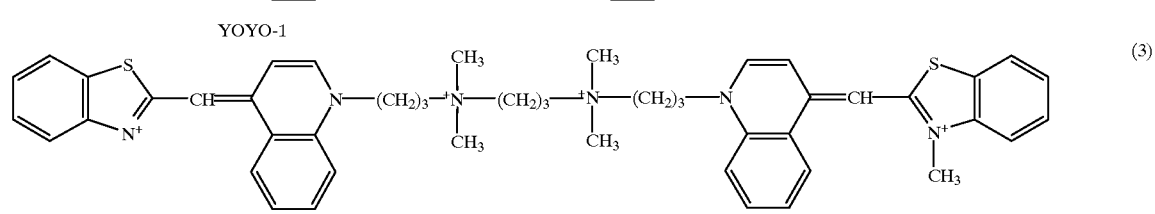

TOTO-1 (3)

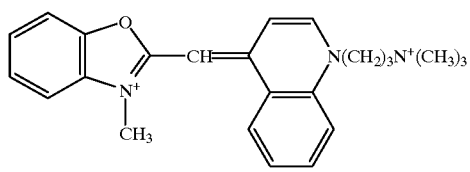
YO-PRO-1 (4)
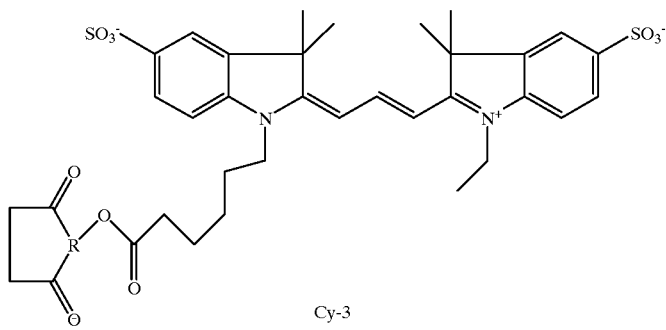
Cy-3 (5)
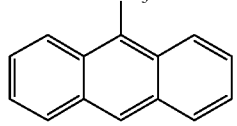
Nile Red (6)
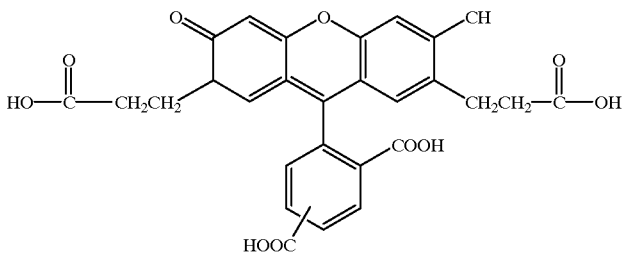
BCECF (7)
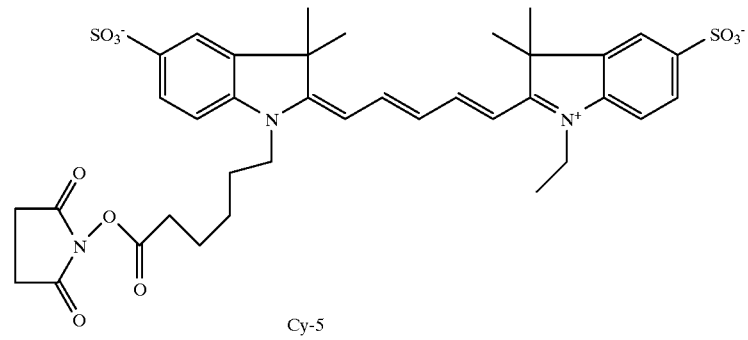
Cy-5 (8)
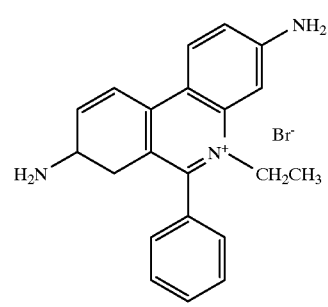
Ethidium Bromide (9)

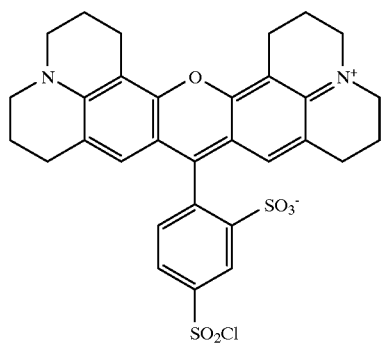

Texas-Red

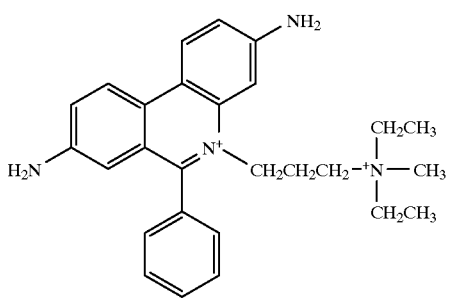

Propidium Iodide

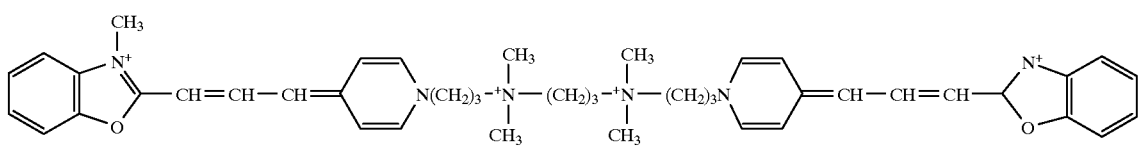

POPO-3

In the present invention, the stimulable phosphor employed for producing a radiation image, an autoradiographic image, a radiographic diffraction image and an electron microscopic image of an object may be of any type insofar as it can store radiation energy or electron beam energy and can be stimulated by an electromagnetic wave to release the radiation energy or electron beam energy stored therein in the form of light. However, a stimulable phosphor which can be stimulated by light having a visible light wavelength is preferably employed. More specifically, preferably employed stimulable phosphors include alkaline earth metal fluorohalide phosphors $(Ba_{1-x}, M^{2+}_x)FX:yA$ (where $M^{2+}$ is at least one alkaline earth metal selected from the group consisting of Mg, Ca, Sr, Zn and Cd; X is at least one halogen selected from the group consisting of Cl, Br and I, A is at least one element selected from the group consisting of Eu, Tb, Ce, Tm, Dy, Pr, He, Nd, Yb and Er; x is equal to or greater than 0 and equal to or less than 0.6 and y is equal to or greater than 0 and equal to or less than 0.2) disclosed in U.S. Pat. No. 4,239,968, alkaline earth metal fluorohalide phosphors SrFX:Z (where X is at least one halogen selected from the group consisting of Cl, Br and I; and Z is at least one of Eu and Ce) disclosed in Japanese Patent Application Laid Open No. 2-276997, europium activated complex halide phosphors $BaFX \cdot xNaX':aEu^{2+}$ (where each of X and X' is at least one halogen selected from the group consisting of Cl, Br and I; x is greater than 0 and equal to or less than 2; and y is greater than 0 and equal to or less than 0.2) disclosed in Japanese Patent Application Laid Open No. 59-56479, cerium activated trivalent metal oxyhalide phosphors MOX:xCe (where M is at least one trivalent metal selected from the group consisting of Pr, Nd, Pm, Sm, Eu, Tb, Dy, Ho, Er, Tm, Yb and Bi; X is at least one halogen selected from the group consisting of Br and I; and x is greater than 0 and less than 0.1) disclosed in Japanese Patent Application Laid Open No. 58-69281, cerium activated rare earth oxyhalide phosphors LnOX:xCe (where Ln is at least one rare earth element selected from the group consisting of Y, La, Gd and Lu; X is at least one halogen selected from the group consisting of Cl, Br, and I; and x is greater than 0 and equal to or less than 0.1) disclosed in U.S. Pat. No. 4,539,137 and europium activated complex halide phosphors $M''FX \cdot aM'X' \cdot bM'''X''_2 \cdot cM'''X'''_3 \cdot xA:yEu^{2+}$ (where M'' is at least one alkaline earth metal selected from the group consisting of Be, Sr and Ca; M' is at least one alkaline metal selected from the group consisting of Li, Na, K, Rb and Cs; M''' is at least one divalent metal selected from the group consisting of Be and Mg; M''' is at least one trivalent metal selected from the group consisting of Al, Ga, In and Tl; A is at least one metal oxide; X is at least one halogen selected from the group consisting of Cl, Br and I; each of X', X" and X'" is at least one halogen selected from the group consisting of F, Cl, Br and I; a is equal to or greater than 0 and equal to or less than 2; b is equal to or greater than 0 and equal to or less than $10^{-2}$; c is equal to or greater than 0 and equal to or less than $10^{-2}$; a+b+c is equal to or greater than $10^{-2}$; x is greater than 0 and equal to or less than 0.5; and y is greater than 0 and equal to or less than 0.2) disclosed in U.S. Pat. No. 4,962,047.

The above and other objects and features of the present invention will become apparent from the following description made with reference to the accompanying drawings.

DESCRIPTION OF THE PREFERRED EMBODIMENTS

Figure 1:
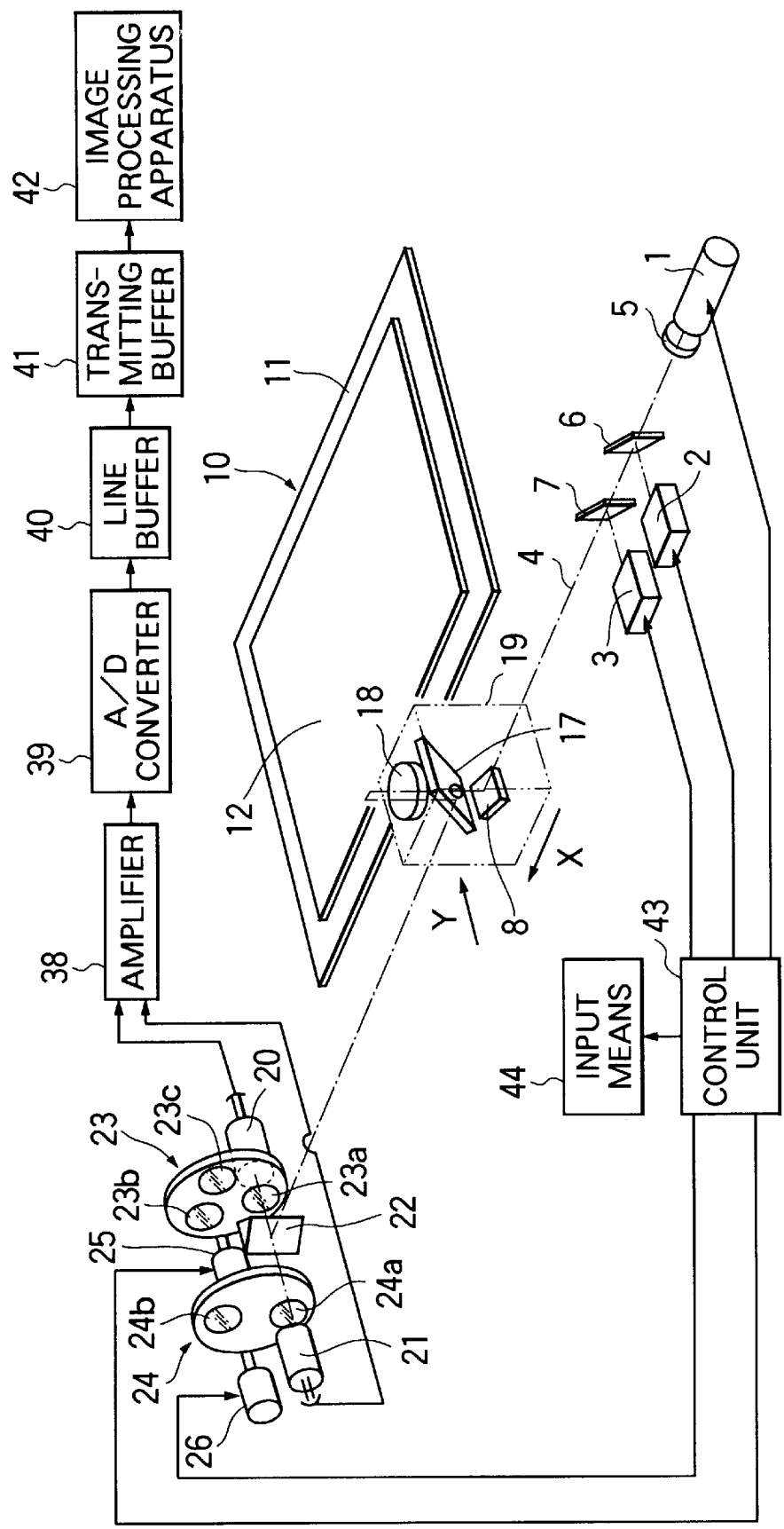
FIG. 1 is a schematic perspective view showing an image reading apparatus which is a preferred embodiment of the present invention.

As shown in FIG. 1, an image reading apparatus includes a first laser stimulating ray source 1 for emitting a laser beam having a wavelength of 633 nm, a second laser stimulating ray source 2 for emitting a laser beam having a wavelength of 532 nm and a third laser stimulating ray source 3 for emitting a laser beam having a wavelength of 473 nm. In this embodiment, the first laser stimulating ray source 1 is constituted by a He—Ne laser beam source and the second laser stimulating ray source 2 and the third laser stimulating ray source 3 are constituted by a second harmonic generation element.

A laser beam 4 emitted from the first laser stimulating ray source 1 passes through a filter 5, thereby cutting light in a wavelength region corresponding to a wavelength region of stimulated emission emitted from the stimulable phosphor sheet in response to stimulation by the laser beam 4 having a wavelength of 633 nm. A first dichroic mirror 6 for transmitting light having a wavelength of 633 nm but reflecting light having a wavelength of 532 nm and a second dichroic mirror 7 for transmitting light having a wavelength longer than 532 nm but reflecting light having a wavelength of 473 nm are provided in the optical path of the laser beam 4 emitted from the first laser stimulating ray source 1. The laser beam 4 emitted from the first laser stimulating source 1 and transmitted through the filter 5 passes through the first dichroic mirror 6 and the second dichroic mirror 7. The laser beam 4 emitted from the second laser stimulating ray source 2 is reflected by the first dichroic mirror 6, thereby changing the direction thereof by 90 degrees, and passes through the second dichroic mirror 7. The laser beam 4 emitted from the third laser stimulating ray source 3 is reflected by dichroic mirror 7. The laser beam 4 emitted from the selected one of the first laser stimulating source 1, the second laser stimulating ray source 2 and the third laser stimulating ray source 3 then enters a mirror 8.

The image reading apparatus according to this embodiment is constituted so as to be able to read out an image of fluorescent dye recorded in a gel support, a transfer support or the like, and a radiation image, an autoradiographic image, a radiographic diffraction image or an electron microscopic image of an object recorded in a stimulable phosphor layer formed on a stimulable phosphor sheet. In FIG. 1, the fluorescent image carrier unit 10 includes a glass plate 11 and a transfer support 12 placed on the glass plate 11 and in which an electrophoresis image of denatured DNA labeled with fluorescent dye is recorded.

The electrophoresis image of denatured DNA labeled with fluorescent dye is recorded in the transfer support 12, for example, in the following manner. First, a plurality of DNA fragments containing a specific gene are separated and distributed on a gel support medium by means of electrophoresis and are denatured by alkali processing to form single-stranded DNA. Then, according to the known Southern blotting method, the gel support and a transfer support 12 are stacked to transfer at least a part of the denatured DNA fragments onto the transfer support 12 and the transferred DNA fragments are fixed on the transfer support by heating and irradiating with an ultraviolet ray. Further, probes prepared by labeling DNA or RNA with fluorescent dye, which is complementary to the DNA containing the specific gene and the denatured DNA fragments on the transfer support 12 are hybridized by heating to form double-stranded DNA fragments or combined DNA and RNA. In this embodiment, since it is intended to detect three kinds of target DNA, three kinds of fluorescent dyes releasing different fluorescent light, for example, Fluorescein, Rhodamine and Cy-5, are used and DNA or RNA which is complementary to the DNA containing DNA of the specific gene is labeled therewith to prepare the probes. Since the denatured DNA fragments are fixed on the transfer support 12 at this time, only the DNA fragments which are complimentary to the probe DNA or probe RNA are hybridized to acquire the fluorescently labeled probe. Then, the probes which have not formed hybrids are removed by washing with a proper solution and only the DNA fragments having a specific gene form hybrids with the fluorescently labeled DNA or RNA on the transfer support 12 to be fluorescently labeled. The thus obtained transfer support records an electrophoresis image of the denatured DNA labeled with fluorescent dye.

Figure 2:
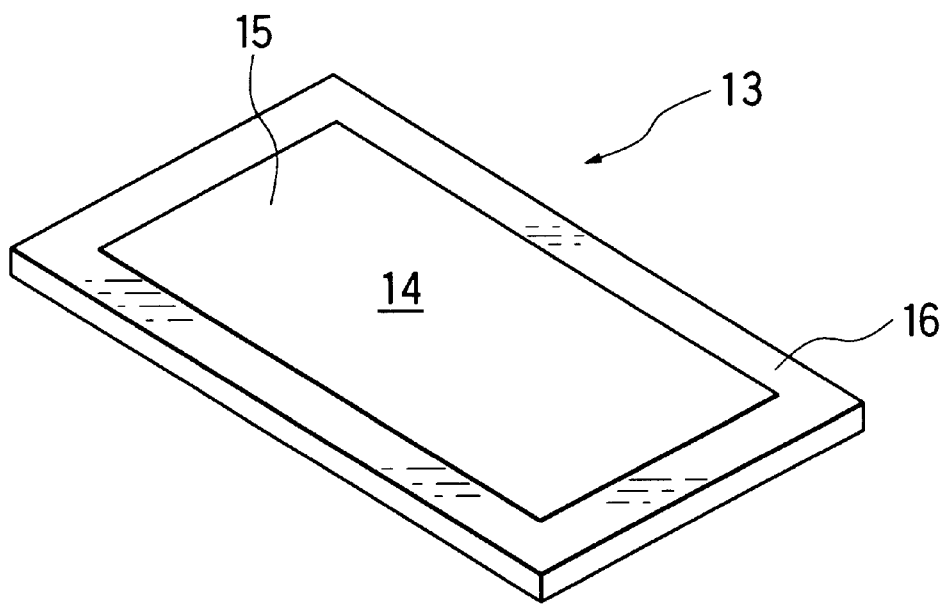
FIG. 2 is a schematic perspective view showing a stimulable phosphor sheet unit.

FIG. 2 is a schematic perspective view showing a stimulable phosphor sheet unit 13.

When a radiation image or electron beam image recorded in a stimulable phosphor layer formed on the stimulable phosphor sheet is to be read, the stimulable phosphor sheet unit 13 is set instead of the fluorescent image carrier unit 10. As shown in FIG. 2, the stimulable phosphor sheet unit 13 includes a stimulable phosphor sheet 15 formed with a stimulable phosphor layer 14 on one surface thereof and a magnetic layer (not shown) on the other surface thereof and a support plate 16 such as an aluminum plate onto which a gum-like magnetic sheet (not shown) is adhered on one surface thereof. The magnetic layer of the stimulable phosphor sheet 15 and the magnet sheet of the support plate 16 are adhered by magnetic force and integrated. In this embodiment, the stimulable phosphor layer 14 formed on the stimulable phosphor sheet 15 records, for example, locational information regarding a radioactively labeled substance contained in a gene produced by the Southern blot hybridization method. Locational information as termed here includes a variety of information relating to the location of radioactive labeled substances, or aggregations thereof, present in a specimen, such as the location, the shape, the concentration, the distribution or combinations thereof.

The locational information regarding a radioactively labeled substance is stored in the stimulable phosphor layer 14 of the stimulable phosphor sheet 15, for example, in the following manner. First, a plurality of DNA fragments containing a specific gene are separated and distributed on a gel support medium by means of electrophoresis and are denatured by alkali processing to form single-stranded DNA. Then, according to the known Southern blotting method, the gel support and a transfer support such as a nitrocellulose filter are placed in layers to transfer at least a part of the denatured DNA fragments onto the transfer support and the transferred DNA fragments are fixed on the transfer support by heating. Further, probes prepared by radioactively labeling DNA or RNA which is complementary to the DNA containing the specific gene and the denatured DNA fragments are hybridized by heating to form double-stranded DNA fragments or combined DNA and RNA. Since the denatured DNA fragments are fixed on the transfer support at this time, only the DNA fragments which are complimentary to the probe DNA or probe RNA are hybridized to acquire the radioactively labeled probe. Then, the probes which have not formed hybrids are removed by washing with a proper solution and only the DNA fragments having a specific gene form hybrids with the radioactively labeled DNA or RNA on the transfer support to be radioactively labeled. The thus obtained transfer support and the stimulable phosphor layer 14 of the stimulable phosphor sheet 15 are stacked for a certain period of time to expose the stimulable phosphor layer 14 and at least a part of the radiation emitted from the radioactively labeled substance on the transfer support is absorbed in the stimulable phosphor layer 14 formed on the stimulable phosphor sheet 15, whereby the locational information regarding the radioactively labeled substance in the specimen is stored in the form of an image in the stimulable phosphor layer 14.

The image reading apparatus according to this embodiment is constituted so that both the fluorescent image carrier unit 10 and the stimulable phosphor sheet unit 13 are kept stationary and the whole surface of the transfer support 12 or the stimulable phosphor layer 14 of the stimulable phosphor sheet 15 can be scanned with a laser beam 4 by moving an optical head 19 provided with a mirror 17 formed with a hole 17a at the center thereof and a convex lens 18 for converging a laser beam 4 onto the image carrier. Fluorescent light released from the transfer support 12 or stimulated emission released from the stimulable phosphor sheet 15 is reflected by the mirror 17 and detected by two photomultipliers 20, 21 whose sensitivity characteristics are different from each other.

Figure 3:
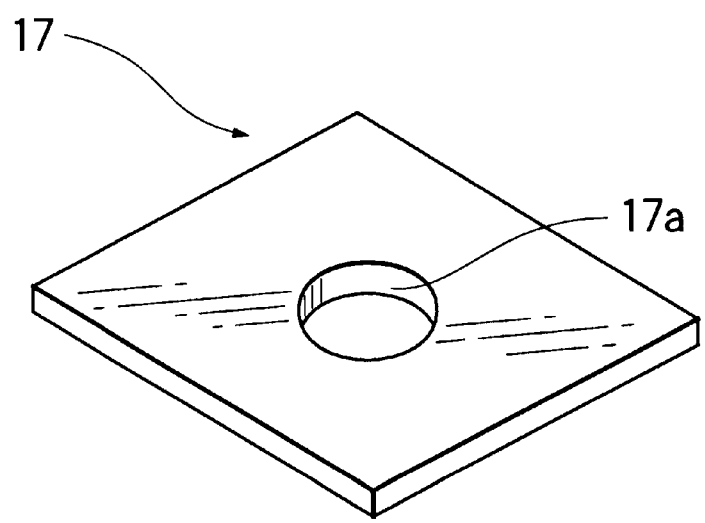
FIG. 3 is a schematic perspective view showing a mirror.

FIG. 3 is a schematic perspective view showing the mirror 17. As shown in FIG. 3, the hole 17a is formed at substantially the center of the mirror 17. The diameter of the hole 17a is determined so as to transmit a laser beam 4 emitted from the first laser stimulating ray source 1, the second laser stimulating ray source 2 or the third laser stimulating ray source 3 therethrough but reflect fluorescent light from the transfer support 12 or stimulated emission from the stimulable phosphor sheet 15 as much as possible.

As shown in FIG. 1, the laser beam 4 reflected by the mirror 8 enters the optical head 19 and passes through the hole 17a of the mirror 17. The laser beam 4 is then converged by the convex lens 18 onto the surface of the transfer support 12 or the stimulable phosphor sheet 15, thereby exciting fluorescent dye or the stimulable phosphor. Fluorescent light from the transfer support 12 or stimulated emission from the stimulable phosphor sheet 15 is transformed to be a parallel light by the convex lens 18, reflected by the mirror 17 in the direction opposite from the first laser stimulating ray source 1, the second laser stimulating ray source 2 and the third laser stimulating ray source 3 to be led to a triangular prism 22. The fluorescent light or stimulated emission is reflected by the triangular prism 22 in two directions and led to the first photomultiplier 20 and the second photomultiplier 21. The first photomultiplier 20 contains a bialkali material based on the compound $K_2CsSb$ prepared by activation with oxygen and cesium and can detect light having a wavelength of 200 nm to 650 nm with high sensitivity. The second photomultiplier 21 contains a bialkali material based on the compound $Na_2KSb$ prepared by activation with a small amount of cesium and can detect light having a wavelength of 200 nm to 850 nm with high sensitivity. Since two photomultipliers 20, 21 which can detect light of different wavelengths with high sensitivity are provided, the first photomultiplier 20 or the second photomultiplier 21 can be selectively used to photoelectrically detect light in accordance with the wavelength of light to be detected and the electrical signal so produced be used as image data, thereby improving the sensitivity of the image reading apparatus.

As shown in FIG. 1, a first filter member 23 and a second filter member 24 are disposed in front of the first photomultiplier 20 and the second photomultiplier 21. The first filter member 23 is constituted by a rotatable disk provided with three filters 23a, 23b and 23c. The filter 23a is used for reading fluorescent light released from fluorescent dye contained in the transfer support 12 upon being excited using the third laser stimulating ray source 3 and has a property to cut off light having a wavelength of 473 nm but transmit light having a wavelength longer than 473 nm. The filter 23b is used for reading fluorescent light released from fluorescent dye contained in the transfer support 12 upon being excited using the second laser stimulating ray source 2 and has a property to cut off light having a wavelength of 532 nm but transmit light having a wavelength longer than 532 nm. The filter 23c is used for reading stimulated emission released from the stimulable phosphor sheet 15 when the stimulable phosphor contained in the stimulable phosphor layer 14 formed on the stimulable phosphor sheet 15 is excited using the first laser stimulating ray source 1 and has a property to allow only light of the wavelength region of the stimulated emission released from the stimulable phosphor to pass through and cuts off light having a wavelength of 633 nm. The second filter member 24 is constituted by a rotatable disk provided with two filters 24a and 24b. The filter 24a is used for reading fluorescent light released from fluorescent dye contained in the transfer support 12 upon being excited using the first laser stimulating ray source 1 and has a property to cut off light having a wavelength of 633 nm but transmit light having a wavelength longer than 633 nm. The filter 24b is used for reading fluorescent light released from fluorescent-dye contained in the transfer support 12 upon being excited using the second laser stimulating ray source 2 and has a property to cut off light having a wavelength of 532 nm but transmit light having a wavelength longer than 532 nm. Therefore, in accordance with the laser stimulating ray source to be employed for exciting fluorescent dye or a stimulable phosphor, namely, the kind of the image carrier and the kind of fluorescent dye, it is possible to detect only light to be detected with high sensitivity by selectively employing the photomultipliers 20, 21, the filters 23a, 23b, 23c and the filters 24a, 24b. The first filter member 23 and the second filter member 24 can be rotated by a first motor 25 and the second motor 26 respectively.

Figure 4:
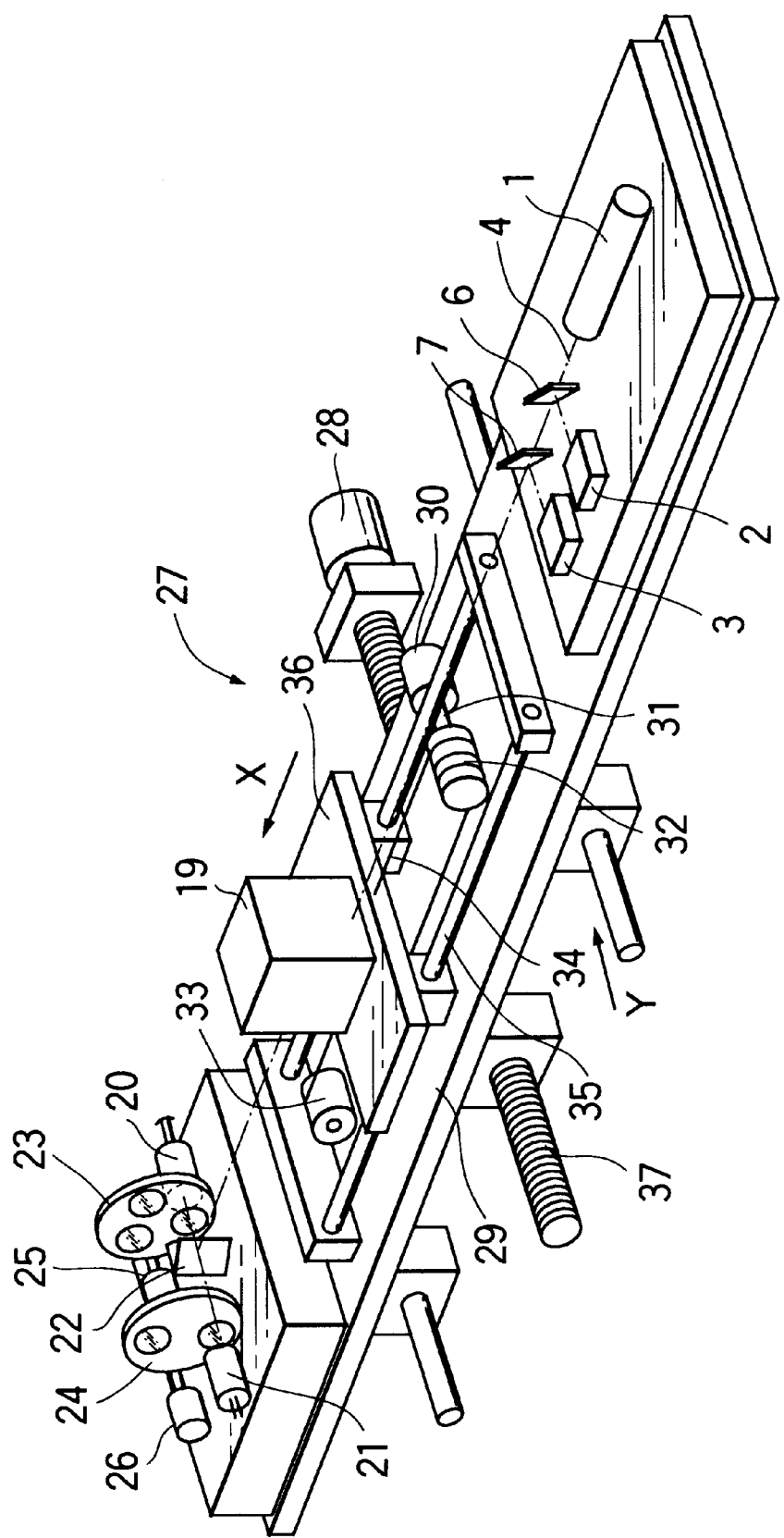
FIG. 4 is a schematic perspective view showing an optical unit.

FIG. 4 is a schematic perspective view showing an optical unit provided with the optical head 19.

As shown in FIG. 4, the optical unit 27 includes a bed 29 movable by a sub-scanning motor 28 in a sub-scanning direction indicated by Y in FIG. 4, a main scanning motor 30 fixed on the bed 29, a drive rotating member 32 fixed to the output shaft 31 of the main scanning motor 30, a driven rotating member 33, a wire 34 wound around the drive rotating member 32 and the driven rotating member 33, an optical head stage 36 to which the ends of the wire 34 are fixed and which is movable in a main scanning direction indicated by X in FIG. 4 while being guided by guide rails 35, and the optical head 19 fixed on the optical head stage 36. A threaded rod 37 is fixed to the output shaft (not shown) of the sub-scanning motor 28 and the bed 29 can be moved in the sub-scanning direction as the sub-scanning motor 28 rotates. The first photomultiplier 20, the second photomultiplier 21, the first filter member 23, the second filter member 24, the first motor 25 and the second motor 26 are fixed on the bed 29.

In the image reading apparatus according to this embodiment, the light photoelectrically detected by the first photomultiplier 20 and the second photomultiplier 21 is converted to an electrical signal, amplified by an amplifier 38 having a predetermined amplifying factor so as to produce an electrical signal of a predetermined level and then input to an A/D converter 39. The electrical signal is converted in the A/D converter 39 to a digital signal with a scale factor suitable for the signal fluctuation width and input to a line buffer 40. The line buffer 40 temporarily stores image data corresponding to one scanning line. When the image data corresponding to one scanning line have been stored in the line buffer 40 in the above described manner, the line buffer 40 outputs the data to a transmitting buffer 41 whose capacity is greater than that of the line buffer 40 and when the transmitting buffer 41 has stored a predetermined amount of the image data, it outputs the image data to an image processing apparatus 42. The image data input to the image processing apparatus 42 are stored in an image data storing means (not shown). The image data are read out from the image data storing means, image-processed as occasion demands and displayed on a display means such as a CRT (not shown) as a visual image or analyzed by an image analyzing apparatus (not shown).

As shown in FIG. 1, the image reading apparatus according to this embodiment further includes a control unit 43 and input means 44 including a keyboard and the like. When a fluorescent image recorded in the transfer support 12 is to be read, an operator inputs the kind of fluorescent dye contained in the transfer support 12 through the input means 44 and when a radiation image recorded in the stimulable phosphor layer 14 formed on the stimulable phosphor sheet 15 is to be read, the operator inputs through the input means 44 that the image carrier is a stimulable phosphor sheet. As a result, the control unit 43 automatically selects one of the first laser stimulating source 1, the second laser stimulating ray source 2 and the third laser stimulating ray source 3 and also selects one of the filters 23a, 23b, 23c, 24a and 24b. The image reading apparatus then starts reading a image.

FIG. 1 shows an example in which an image of fluorescent dye recorded in the transfer support 12 is to be read. In the case where the image of fluorescent dye is to be read, the kind of fluorescent dye is input by the operator through the input means 44 and in accordance with the input instruction signal, the control unit 43 selects one of the first photomultiplier 20 and the second photomultiplier 21 and drives one of the first motor 25 and the second motor 26 to rotate one of the first filter member 23 and the second filter member 24 so that one of the filters 23a, 23b and 23c is positioned in front of the first photomultiplier 20 or that one of the filters 24a and 24b is positioned in front of the second photomultiplier 21. The control unit 43 then activates one among the first laser stimulating ray source 1, the second laser stimulating ray source 2 and the third laser stimulating ray source 3. A laser beam 4 emitted from the selected one of the first laser stimulating ray source 1, the second laser stimulating ray source 2 and the third laser stimulating ray source 3 and reflected by the mirror 8 passes through the hole 17a of the mirror 17 and is converged by the convex lens 18 onto the surface of the transfer support 12 on the glass plate 11. As a result, fluorescent dye contained in the transfer support 12 is excited to release fluorescent light.

The fluorescent light released from the fluorescent dye contained in the transfer support 12 is transformed to be parallel light by the convex lens 18 and reflected by the mirror 17 in the direction opposite from the first laser stimulating ray source 1, the second laser stimulating ray source 2 and the third laser stimulating ray source 3. The fluorescent light impinges on the triangular prism 22 and is reflected in two directions.

In this embodiment, DNA fragments of the target gene are labeled with three kinds of fluorescent dye, namely, Fluorescein, Rhodamine B and Cy-5, and a fluorescent image is recorded. When the fluorescent images of DNA fragments of the target gene labeled with Cy-5, Rhodamine B and Fluorescein are read in this order, the operator inputs through the input means 44 an instruction requesting that the fluorescent images be subsequently read and the kinds of fluorescent dye subsequently read.

When such instruction signals are input through the input means 44, in accordance with the instruction signals, the control unit 43 outputs a drive signal to the second motor 26 to rotate the second filter member 24 so that the filter 24a is positioned in front of the light receiving surface of the second photomultiplier 21. The control unit 43 then activates the first laser stimulating ray source 1. As a result, a laser beam 4 having a wavelength of 633 nm is emitted from the first laser stimulating ray source 1 and passes through the dichroic mirrors 6, 7. The laser beam 4 is then reflected by the mirror 8 and enters the optical head 19. The laser beam 4 entering the optical head 19 passes through the hole 17a of the mirror 17 and is converged by the convex lens 18 onto the transfer support 12. Since the optical head 19 is moved by the main scanning motor 30 in the main scanning direction indicated by X in FIGS. 1 and 4, while the bed 29 on which the optical head 19 is mounted is moved by the sub-scanning motor 28 in the sub-scanning direction indicated by Y in FIGS. 1 and 4, the whole surface of the transfer support 12 is scanned with the laser beam 4 having a wavelength of 633 nm. As a result, Cy-5 contained in the transfer support 32 is excited to release fluorescent light whose peak wavelength is 667 nm.

The fluorescent light released from Cy-5 contained in the transfer support 12 is reflected by the mirror 17 and further reflected by the triangular mirror 22 in two directions to be photoelectrically detected by the first photomultiplier 20 and the second photomultiplier 21.

When an instruction signal requesting that the image of fluorescent dye Cy-5 be read first has been input through the input means 44, the control unit 43 forwards only an electrical signal produced by photoelectrically detecting the fluorescent light by the second photomultiplier 21 to the line buffer 40 via the amplifier 38 and the A/D converter 39 and image data corresponding to one scanning line are stored in the line buffer 40. When the image data corresponding to one scanning line have been stored in the line buffer 40, the image data are output from the line buffer 40 to the transmission buffer 41.

The image data obtained by detecting the fluorescent light released from Cy-5 are output from the transmission buffer 41 to the image processing apparatus 42 and a visual image is displayed on a display means such as a CRT. The thus displayed image contains the image of DNA labeled with Cy-5 and the image data produced in this manner are stored in an image data storing means (not shown) or analyzed by an image analyzing apparatus (not shown).

When the excitation by the first laser stimulating ray source 1 has been completed, the control unit 43 outputs a drive signal to the sub-scanning motor 28 to return the bed 29 to its original position and outputs a drive signal to the main scanning motor 30 to return the optical head 19 to its original position. The control unit 43 then outputs a drive signal to the first motor 25 to rotate the first filter member 23 so that the filter 23b is positioned in front of the light receiving surface of the first photomultiplier 21 and activates the second laser stimulating ray source 2. As a result, a laser beam 4 having a wavelength of 532 nm is emitted from the second laser stimulating ray source 2 and is reflected by the dichroic mirror 6. After the laser beam 4 has passed through the dichroic mirror 7, it is then reflected by the mirror 8 and enters the optical head 19. The laser beam 4 entering the optical head 19 passes through the hole 17a of the mirror 17 and is converged by the convex lens 18 onto the transfer support 12. Since the optical head 19 is moved by the main scanning motor 30 in the main scanning direction indicated by X in FIGS. 1 and 4, while the bed 29 on which the optical head 19 is mounted is moved by the sub-scanning motor 28 in the sub-scanning direction indicated by Y in FIGS. 1 and 4, the whole surface of the transfer support 12 is scanned with the laser beam 4 having a wavelength of 532 nm. As a result, Rhodamine B contained in the transfer support 12 is excited to release fluorescent light whose peak wavelength is 605 nm.

The fluorescent light released from Rhodamine B contained in the transfer support 12 is reflected by the mirror 17 and further reflected by the triangular mirror 22 in two directions to be photoelectrically detected by the first photomultiplier 20 and the second photomultiplier 21.

When an instruction signal requesting that the image of fluorescent dye Rhodamine B be read after reading the fluorescent image of Cy-5 has been input through the input means 44, the control unit 43 forwards only an electrical signal produced by photoelectrically detecting the fluorescent light by the first photomultiplier 20 to the line buffer 40 via the amplifier 38 and the A/D converter 39 and image data corresponding to one scanning line are stored in the line buffer 40. When the image data corresponding to one scanning line have been stored in the line buffer 40, the image data are output from the line buffer 40 to the transmission buffer 41.

The image data obtained by detecting the fluorescent light released from Rhodamine B are output from the transmission buffer 41 to the image processing apparatus 42 and a visual image is displayed on a display means such as a CRT. The thus displayed image contains the image of DNA labeled with Rhodamine B and the image data produced in this manner are stored in an image data storing means (not shown) or analyzed by an image analyzing apparatus (not shown).

When the excitation by the second laser stimulating ray source 2 has been completed, the control unit 43 outputs a drive signal to the sub-scanning motor 28 to return the bed 29 to its original position and outputs a drive signal to the main scanning motor 30 to return the optical head 19 to its original position. The control unit 43 then outputs a drive signal to the first motor 25 to rotate the first filter member 23 so that the filter 23a is positioned in front of the light receiving surface of the first photomultiplier 20 and activates the third laser stimulating ray source 3. As a result, a laser beam 4 having a wavelength of 473 nm is emitted from the third laser stimulating ray source 3 and is reflected by the dichroic mirror 7. The laser beam 4 is then reflected by the mirror 8 and enters the optical head 19. The laser beam 4 entering the optical head 19 passes through the hole 17a of the mirror 17 and is converged by the convex lens 18 onto the transfer support 12. Since the optical head 19 is moved by the main scanning motor 30 in the main scanning direction indicated by X in FIGS. 1 and 4, while the bed 29 on which the optical head 19 is mounted is moved by the sub-scanning motor 28 in the sub-scanning direction indicated by Y in FIGS. 1 and 4, the whole surface of the transfer support 12 is scanned with the laser beam 4 having a wavelength of 473 nm. As a result, Fluorescein contained in the transfer support 12 is excited to release fluorescent light whose peak wavelength is 530 nm. In this embodiment, since the fluorescent dye is stimulated using the third laser stimulating ray source 3 for emitting a laser beam 4 having a wavelength of 473 nm, the strength of the stimulating ray is higher than that emitted from an LED and, therefore, it is possible to generate a sufficiently great amount of fluorescent light from the fluorescent dye.

The fluorescent light released from Fluorescein contained in the transfer support 12 is reflected by the mirror 17 and further reflected by the triangular mirror 22 in two directions to be photoelectrically detected by the first photomultiplier 20 and the second photomultiplier 21.

When an instruction signal requesting that the image of fluorescent dye Fluorescein be read last has been input through the input means 44, the control unit 43 forwards only an electrical signal produced by photoelectrically detecting the fluorescent light by the first photomultiplier 20 to the line buffer 40 via the amplifier 38 and the A/D converter 39 and image data corresponding to one scanning line are stored in the line buffer 40. When the image data corresponding to one scanning line have been stored in the line buffer 40, the image data are output from the line buffer 40 to the transmission buffer 41.

The image data obtained by detecting the fluorescent light released from Fluorescein are output from the transmission buffer 41 to the image processing apparatus 42 and a visual image is displayed on a display means such as a CRT. The thus displayed image contains the image of DNA labeled with Fluorescein and the image data produced in this manner are stored in an image data storing means (not shown) or analyzed by an image analyzing apparatus (not shown).

On the other hand, when a radiation image, an autoradiographic image, a radiographic diffraction image or an electron microscopic image of an object recorded in a stimulable phosphor layer 14 of the stimulable phosphor sheet 15 is read out, instead of the fluorescent image carrier unit 10, the stimulable phosphor sheet unit 13 shown in FIG. 2 is set in the image reading apparatus and the stimulable phosphor sheet 15 formed with the stimulable phosphor layer 14 recording locational information regarding a radioactively labeled substance contained in a gene produced by the Southern blot hybridization method is scanned with the laser beam 4.

When a radiation image is read from the stimulable phosphor sheet 15 recording locational information regarding a radioactively labeled substance in a specimen, the operator inputs an instruction that the image carrier is a stimulable phosphor sheet 15. As a result, the control unit 43 outputs a drive signal to the first motor 25 to rotate the first filter member 23 so that the filter 23c is positioned in front of the light receiving surface of the first photomultiplier 20. The control unit 43 then activates the first laser stimulating ray source 1. As a result, a laser beam emitted from the first laser stimulating ray source 1 passes through the hole 17a formed in the mirror 17 of the optical head 19 and is converged by the convex lens 18 onto the surface of the stimulable phosphor layer 14 formed on the stimulable phosphor sheet 15, whereby the surface of the stimulable phosphor layer 14 is scanned with the laser beam 4 having a wavelength of 633 nm in the same manner as the transfer support 12 and the stimulable phosphor contained in the stimulable phosphor layer 14 is excited by the laser beam 4 to release stimulated emission. The stimulated emission is transformed to parallel light by the convex lens 18 and is reflected by the mirror 17 to be led to the triangular prism 22 along the path different from that from the laser stimulating ray source to the stimulable phosphor sheet 15. The stimulated emission is further reflected by the triangular prism 22 in two directions and photoelectrically detected by the first photomultiplier 20 and the second photomultiplier 21.

When the instruction that the image carrier is a stimulable phosphor 15 has been input through the input means 44, the control unit 43 forwards only an electrical signal produced by photoelectrically detecting the stimulated emission by the first photomultiplier 20 to the line buffer 40 via the amplifier 38 and the A/D converter 39 and image data corresponding to one scanning line are stored in the line buffer 40. When the image data corresponding to one scanning line have been stored in the line buffer 40, the image data are output from the line buffer 40 to the transmission buffer 41.

The image data obtained by detecting the stimulated emission released from the stimulable phosphor contained in the stimulable phosphor layer 14 formed on the stimulable phosphor sheet 15 are output from the transmission buffer 41 to the image processing apparatus 42 and a visual image is displayed on a display means such as a CRT. The thus displayed image contains the image of DNA labeled with the radioactively labeled substance and the image data produced in this manner are stored in an image data storing means (not shown) or analyzed by an image analyzing apparatus (not shown).

According to the above described embodiment, the laser beam 4 emitted from the first laser stimulating ray source 1, the second laser stimulating ray source 2 or the third laser stimulating ray source 3 passes through the hole 17a formed in the mirror 17 of the optical head 19 and is converged by the convex lens 18 onto the surface of the transfer support 12 or the stimulable phosphor layer 14. The surface of the transfer support 12 or the stimulable phosphor layer 14 is scanned with the laser beam 4 by moving the optical head 19 in both the main scanning direction and the sub-scanning direction, whereby fluorescent light or stimulated emission is released from the transfer support 12 or the stimulable phosphor layer 14. The fluorescent light or the stimulated emission is reflected by the mirror 17 in the direction opposite from the first laser stimulating ray source 1, the second laser stimulating ray source 2 and the third laser stimulating ray source 3 and photoelectrically detected by the first photomultiplier 20 and the second photomultiplier 21. Therefore, according to this embodiment, even if the second harmonic generation element capable of emitting a stimulating ray having high strength is used instead of an LED as the second laser stimulating ray source 2 or the third laser stimulating ray source 3, the surface of the transfer support 12 or the stimulable phosphor layer 14 can be scanned with the laser beam 4 with a simple structure and at high speed and, therefore, detection sensitivity can be markedly improved. Furthermore, since fluorescent dye contained in the transfer support 12 is excited using the first laser stimulating ray source 1 for emitting a laser beam 4 having a wavelength of 633 nm, the second laser stimulating ray source 2 for emitting a laser beam 4 having a wavelength of 532 nm and the third laser stimulating ray source 3 for emitting a laser beam 4 having a wavelength of 473 nm and a fluorescent image recorded in the transfer support 12 is read by a single image reading apparatus, it is possible to label a specimen with fluorescent dye excitable with a laser beam 4 having a wavelength of 633 nm, fluorescent dye excitable with a laser beam 4 having a wavelength of 532 nm and fluorescent dye excitable with a laser beam 4 having a wavelength of 473 nm and the utility of the fluorescence detecting system can be improved. Further, both the electrophoresis image of DNA labeled with fluorescent dye and recorded in the transfer support 32 and the electrophoresis image of DNA labeled with the radioactively labeled substance and recorded in the stimulable phosphor layer 41 formed on the stimulable phosphor sheet 42 can be read by a single image reading apparatus. The efficiency is therefore high. Further, since the first photomultiplier 20 and the second photomultiplier 21 differing in sensitivity are provided, fluorescent light and stimulated emission can be detected with high sensitivity. Furthermore, when the kind of fluorescent dye is input through the input means 44, the control unit 43 selects whichever of the first photomultiplier 20 and the second photomultiplier 21 is suitable for detecting fluorescent light released from the specified fluorescent dye and rotates the first filter member 23 or the second filter member 24 to select a filter suitable for detecting fluorescent light released from the specified fluorescent dye from among the filters 23a, 23b, 23c and 24a, 24b and position it in front of the first photomultiplier 20 or the second photomultiplier 21. The control unit 43 then selects a laser stimulating ray source suitable for exciting the specified fluorescent dye forming a fluorescent image to be read from among the first laser stimulating ray source 1, the second laser stimulating ray source 2 and the third laser stimulating ray source 3 and causes it to emit a laser beam 4, thereby reading a fluorescent image. Or when an instruction that the image carrier is a stimulable phosphor sheet 15 is input through the input means 44, the control unit 430 selects the first photomultiplier 20 suitable for detecting stimulated emission and rotates the first filter member 23 to position the filter 23c in front of the first photomultiplier 20. The control unit 43 then activates the first laser stimulating ray source 1 suitable for exciting the stimulable phosphor and causes it to emit a laser beam 4, thereby reading a radiation image. Therefore, the operation is very simple and it is possible to eliminate the risk of erroneously activating the second laser stimulating ray source 2 or the third laser stimulating ray source 3 when a radiation image recorded in the stimulable phosphor layer 14 formed on the stimulable phosphor sheet 15 is to be read. It is therefore possible to eliminate the risk of such an error causing a part of radiation energy stored in the stimulable phosphor layer 14 to be released so that the radiation image cannot be accurately read or cannot be read at all as the case may be.

The present invention has thus been shown and described with reference to specific embodiments. However, it should be noted that the present invention is in no way limited to the details of the described arrangements but changes and modifications may be made without departing from the scope of the appended claims.

For example, in the above described embodiment, the laser beam 4 emitted from the first laser stimulating ray source 1, the second laser stimulating ray source 2 or the third laser stimulating ray source 3 passes through the hole 17a formed in the mirror 17 and is converged by the convex lens 18 onto the surface of the transfer support 12 or the stimulable phosphor layer 14. Fluorescent light released from the transfer support 12 or stimulated emission released from the stimulable phosphor layer 14 is reflected by the mirror 17 in the direction opposite from the first laser stimulating ray source 1, the second laser stimulating ray source 2 and the third laser stimulating ray source 3 and photoelectrically detected. However, it is sufficient to form a portion for transmitting a laser beam 4 in the mirror 17 by providing a coating allowing a laser beam 4 to pass therethrough or a total reflection coating on the mirror 17 except at a portion through which a laser beam 4 passes and the like but it is not necessary to form the hole 17a in the mirror 17.

Further, in the above described embodiment, fluorescent light or stimulated emission is lead using the triangular prism 22 to the first photomultiplier 20 and the second photomultiplier 21 and the control unit 43 inputs only one of the electrical signals produced by the first photomultiplier 20 and the second photomultiplier 21 as image data. Instead of the triangular prism 22, however, it is possible to adopt a configuration provided with a rotatable mirror which can be selectively positioned in a first position where it leads fluorescent light or stimulated emission to the first photomultiplier 20 and in a second position where it leads fluorescent light or stimulated emission to the second photomultiplier 21, and wherein the control unit 43 rotates the mirror in accordance with the wavelength of fluorescent light or stimulated emission to be detected to locate it in the first position or the second position, thereby leading the fluorescent light or the stimulated emission to the first photomultiplier 20 or the second photomultiplier 21 and that an electrical signal produced by the first photomultiplier 20 or the second photomultiplier 21 is input as image data. This configuration is desirable because it enables the amount of detected fluorescent light or stimulated emission to be doubled.

Furthermore, in the above described embodiment, the electrophoresis image of gene obtained by Southern blot hybridization method is recorded in the transfer support 32 in accordance with a fluorescent detection system and is recorded in the stimulable phosphor layer 41 formed on the stimulable phosphor sheet 42 in accordance with the autoradiographic system and these images are photoelectrically read out. However, the present invention is not limited to such image reading but can also be applied to various other types of image reading. Specifically, the present invention can also be applied to reading of other images of fluorescent substances recorded in a gel support or a transfer support in accordance with the fluorescent detection system or images for the separation or identification of protein or the estimation of molecular weight or properties of protein or the like, autoradiographic images of a protein produced by thin layer chromatography (TLC) and recorded in the stimulable phosphor layer 41 formed on the stimulable phosphor sheet 42, an autoradiographic image produced by polyacrylamide gel electrophoresis for the separation or identification of protein or the estimation of molecular weight or properties of protein or the like and recorded in the stimulable phosphor layer 41 formed on the stimulable phosphor sheet 42, and an autoradiographic image recorded in the stimulable phosphor layer 41 formed on the stimulable phosphor sheet 42 for studying the metabolism, absorption, excretion path and state of a substance introduced into a test mouse. Further, the present invention is applicable to reading of an electron beam transmission image or an electron beam diffraction image of a metal or nonmetal produced by an electron microscope and an electron microscope image of tissue of an organism recorded in the stimulable phosphor layer 41 formed on the stimulable phosphor sheet 42, and a radiographic diffraction image of a metal or nonmetal recorded in the stimulable phosphor layer 41 formed on the stimulable phosphor sheet 42.

Further, in the above described embodiment, although the image reading apparatus includes the second laser stimulating ray source 2, the second laser stimulating ray source 2 is not absolutely necessary.

Furthermore, in the above described embodiment, although the He—Ne laser is used as the first laser stimulating ray source 1, a semiconductor laser diode may be employed instead of the He—Ne laser.

Moreover, in the above described embodiment, although the laser beam source for emitting a laser beam 4 having a wavelength of 633 nm, the laser beam source for emitting a laser beam 4 having a wavelength of 532 nm and the laser beam source for emitting a laser beam 4 having a wavelength of 473 nm are respectively used as the first laser stimulating ray source 1, the second laser stimulating ray source 2 and the third laser stimulating ray source 3, a laser beam source for emitting a laser beam 4 having a wavelength of 635 nm may be used for the first laser stimulating ray source 1 instead of the laser beam source for emitting a laser beam 4 having a wavelength of 633 nm and a laser beam source for emitting a laser beam 4 having a wavelength of 530 nm to 540 nm and a laser beam source for emitting a laser beam 4 having a wavelength of 470 nm to 480 nm may be used for the second laser stimulating ray source 2 and the third laser stimulating ray source 3 respectively.

Further, in the above described embodiment, fluorescent dye is excited with the laser beam 4 having a wavelength of 532 nm and fluorescent light released from the fluorescent dye and having the peak wavelength of 605 nm is photoelectrically detected by the first photomultiplier 20. However, it is not necessary for the fluorescent light released from fluorescent dye excitable with the laser beam 4 having a wavelength of 532 nm to be photoelectrically detected by the first photomultiplier 20. In the case where the peak wavelength of the fluorescent light released from fluorescent dye excitable with the laser beam 4 having a wavelength of 532 nm is located on longer wavelength side, it may be photoelectrically detected by the second photomultiplier 21 and this is more advantageous.

Furthermore, in the above described embodiment, when a fluorescent image recorded in the transfer support 12 is read, the kind of fluorescent dye is input through the input means 44 and when a radiation image recorded in the stimulable phosphor layer 14 formed on the stimulable phosphor sheet 15 is read, an instruction that the image carrier is a stimulable phosphor sheet is input through the input means 44, whereby the control unit 43 automatically selects one of the laser stimulating ray sources 1, 2, 3, the first photomultiplier 20 or the second photomultiplier 21 and one of the filters 23a, 23b, 23c, 24a, 24b. However, the kinds of instruction signals for causing the control unit 43 to effect such automatic selection can be arbitrarily determined and it is not necessary to input the kinds of fluorescent dye or that the image carrier is a stimulable phosphorsheet.

According to the present invention, it is possible to provide an image reading apparatus comprising a plurality of laser stimulating ray sources for emitting laser beams having different wavelengths and capable of being used for a radiation diagnosis system, an autoradiographic system, an electron microscope detecting system and a radiation diffraction image detecting system using a stimulable phosphor and a fluorescence detecting system and accurately reading an image with a simple structure.

I claim:

1. An image reading apparatus comprising:
   at least first and second laser stimulating ray sources for emitting laser beams having different wavelengths;
   laser beam scanning means for scanning an image carrier carrying an image with the laser beam emitted from a selected one of the laser stimulating ray sources; and
   light detecting means for photoelectrically detecting light released from the image carrier,
   wherein the laser stimulating ray sources are remotely located from the laser beam scanning means such that the laser stimulating ray sources do not move with the laser beam scanning means in at least one direction,
   wherein the laser beam scanning means includes a single platform for scanning the laser beam from the remotely located laser stimulating ray sources onto the image carrier in a main scanning direction and a subscanning direction,
   wherein the laser beam scanning means is further provided with a laser beam transmission portion for transmitting the laser beam therethrough,
   wherein the the laser beam scanning means includes a mirror means for reflecting light released from the image carrier to lead the light to the light detecting means, and
   wherein the mirror means and the laser beam transmission portion are located on the single platform.

2. An image reading apparatus in accordance with claim 1 wherein the laser beam transmission portion is formed by a hole.

3. An image reading apparatus in accordance with claim 2 wherein the at least two laser stimulating ray sources include a first laser stimulating ray source for emitting a laser beam having a wavelength of 633 nm or 635 nm and a second laser stimulating ray source for emitting a laser beam having a wavelength of 470 nm to 480 nm.

4. An image reading apparatus in accordance with claim 3 wherein the image carrier to be scanned with the laser beam emitted from the first laser stimulating ray source is constituted by a carrier carrying an image of fluorescent substances or a stimulable phosphor sheet containing a stimulable phosphor recording an image selected from the group consisting of a radiation image, an autoradiographic image, a radiographic diffraction image and an electron microscope image of an object and the image carrier to be scanned with the laser beam emitted from the second laser stimulating ray source is constituted by a carrier carrying an image of fluorescent substances.

5. An image reading apparatus in accordance with claim 4 which further comprises a third laser stimulating ray source for emitting a laser beam having a wavelength of 530 to 540 nm.

6. An image reading apparatus in accordance with claim 5 wherein the image carrier to be scanned with the laser beam emitted from the third laser stimulating ray source is constituted by a carrier carrying an image of fluorescent substances.

7. An image reading apparatus in accordance with claim 1 wherein the laser beam transmission portion is formed by applying a coating capable of transmitting the stimulating ray therethrough.

8. An image reading apparatus in accordance with claim 7 wherein the at least two laser stimulating ray sources include a first laser stimulating ray source for emitting a laser beam having a wavelength of 633 nm or 635 nm and a second laser stimulating ray source for emitting a laser beam having a wavelength of 470 nm to 480 nm.

9. An image reading apparatus in accordance with claim 8 wherein the image carrier to be scanned with the laser beam emitted from the first laser stimulating ray source is constituted by a carrier carrying an image of fluorescent substances or a stimulable phosphor sheet containing a stimulable phosphor recording an image selected from the group consisting of a radiation image, an autoradiographic image, a radiographic diffraction image and an electron microscope image of an object and the image carrier to be scanned with the laser beam emitted from the second laser stimulating ray source is constituted by a carrier carrying an image of fluorescent substances.

10. An image reading apparatus in accordance with claim 9 which further comprises a third laser stimulating ray source for emitting a laser beam having a wavelength of 530 to 540 nm.

11. An image reading apparatus in accordance with claim 10 wherein the image carrier to be scanned with the laser beam emitted from the third laser stimulating ray source is constituted by a carrier carrying an image of fluorescent substances.

12. An image reading apparatus in accordance with claim 1 wherein the at least two laser stimulating ray sources include a first laser stimulating ray source for emitting a laser beam having a wavelength of 633 nm or 635 nm and a second laser stimulating ray source for emitting a laser beam having a wavelength of 470 nm to 480 nm.

13. An image reading apparatus in accordance with claim 12 wherein the image carrier to be scanned with the laser beam emitted from the first laser stimulating ray source is constituted by a carrier carrying an image of fluorescent substances or a stimulable phosphor sheet containing a stimulable phosphor recording an image selected from the group consisting of a radiation image, an autoradiographic image, a radiographic diffraction image and an electron microscope image of an object and the image carrier to be scanned with the laser beam emitted from the second laser stimulating ray source is constituted by a carrier carrying an image of fluorescent substances.

14. An image reading apparatus in accordance with claim 13 which further comprises a third laser stimulating ray source for emitting a laser beam having a wavelength of 530 to 540 nm.

15. An image reading apparatus in accordance with claim 14 wherein the image carrier to be scanned with the laser beam emitted from the third laser stimulating ray source is constituted by a carrier carrying an image of fluorescent substances.

16. The image forming apparatus according to claim 1, wherein the light detecting means includes a reflecting means reflecting the received light to at least one of a first photomultiplier and a second photomultiplier.

17. The image forming apparatus according to claim 16, wherein the reflecting means comprises a triangular prism.

18. The image forming apparatus according to claim 16, wherein the reflecting means comprises a mirror.

19. The image forming apparatus according to claim 16, further comprising first and second selectable filter means, each including a plurality of filters, wherein said first selectable filter means is disposed between the reflecting means and the first photomultiplier and wherein said second selectable filter means is disposed between the reflecting means and the second photomultiplier, and wherein at least one of 1) said first selectable filter means and first multiplier and 2) said second selectable filter means and said second multiplier is operable depending on which of said laser stimulating ray sources is selected.

20. The image reading apparatus of claim 1, wherein the light detecting means is located opposite to the first and second laser stimulating ray sources relative to the laser beam scanning means.

* * * * *